United States Patent
Grant et al.

(10) Patent No.: US 7,449,038 B2
(45) Date of Patent: Nov. 11, 2008

(54) METHODS AND SYSTEMS FOR DETECTING BAGHOUSE FILTER LEAKS

(75) Inventors: John Wesley Grant, Gardnerville, NV (US); Donald R. Pegelow, Fallmouth, VA (US)

(73) Assignee: General Electric Company, Schenectady, NY (US)

(*) Notice: Subject to any disclaimer, the term of this patent is extended or adjusted under 35 U.S.C. 154(b) by 476 days.

(21) Appl. No.: 11/163,095

(22) Filed: Oct. 5, 2005

(65) Prior Publication Data

US 2007/0084339 A1   Apr. 19, 2007

(51) Int. Cl.
*B01D 46/02* (2006.01)

(52) U.S. Cl. ............... 55/309; 55/312; 55/341.1; 95/25; 95/273; 96/418; 96/419; 73/28.01

(58) Field of Classification Search ............ 55/309, 55/312, 341.1; 95/25, 273; 96/418, 419; 73/28.01
See application file for complete search history.

(56) References Cited

U.S. PATENT DOCUMENTS 3,277,238 A    10/1966  Sharp
3,865,561 A    2/1975   Osborn
3,877,899 A *  4/1975   Bundy et al. ............... 96/428
3,960,001 A *  6/1976   Hayes ....................... 73/40.7
4,304,492 A    12/1981  Fox
4,999,032 A    3/1991   Wright ........................ 55/97
5,324,344 A *  6/1994   Broyan et al. .............. 95/25

FOREIGN PATENT DOCUMENTS

GB    2390675    1/2004
WO    0161854    7/2001

\* cited by examiner

*Primary Examiner*—Jason M Greene
*Assistant Examiner*—Minh-Chau T Pham
(74) *Attorney, Agent, or Firm*—Sutherland Asbill & Brennan LLP

(57) ABSTRACT

A method of detecting leaks in the filter bags of a baghouse filter chamber that includes determining when the filter bags have been cleaned and, during a post-cleaning period after the cleaning of the filter bags, determining whether the opacity level of the exhaust of the baghouse filter chamber exceeds a predefined opacity limit. The determining whether the opacity level of the exhaust of the baghouse filter chamber exceeds a predefined opacity limit may include monitoring the opacity level of the exhaust of the baghouse filter chamber with an opacity sensor during the post-cleaning period and comparing the opacity readings during the post-cleaning period with the value of the predefined opacity limit.

20 Claims, 2 Drawing Sheets

METHODS AND SYSTEMS FOR DETECTING BAGHOUSE FILTER LEAKS

TECHNICAL FIELD

This present invention relates generally to methods and systems for detecting baghouse filter leaks. More specifically, the present invention relates to methods and systems for using opacity measurements to determine if a leak in a baghouse filter is present.

BACKGROUND OF THE INVENTION

Methods and systems for identifying leaks in the filter bags of baghouse filter systems have been described. These known methods and systems have encountered significant issues in accurately identifying filter bag leaks and, thus, are often unreliable. In general, these known methods and systems operate by sensing increased air flow through individual baghouse filter bags, as this condition can be indicative of a leak in the bag fabric. If a leak in the filter bag fabric is correctly identified, the leaking filter bag may be closed off to prevent leakage of unfiltered air with pollutants into the atmosphere.

As stated, though, significant issues exist that prevent the reliable use of increased air flow through a filter bag as the primary leak predictor. For example, under normal conditions the flow of air through baghouse filtering systems creates zones of turbulence, eddies, laminar flow, calm and other flow conditions that change in unpredictable patterns as the volume of air moving through the baghouse filtering system is altered. At a certain volume a particular filter bag may display a high flow rate through it, while an increase in the overall volume through the baghouse filter system might actually decrease the flow rate through that particular filter bag. Further, the changing or cleaning of the filter bags may modify the flow patterns within the baghouse chamber. These unpredictable flow patterns make it difficult to detect those changes in flow rate that are caused by a filter bag leak. This, of course, hinders the ability to use flow volume characteristics to predict reliably baghouse filter leaks.

As a result, filter bags may be identified as leaking that are not, or baghouse filters that are leaking may be missed. Further, these characteristics make it very difficult to detect minor leaks. This may lead to inefficiencies in operating and maintaining the baghouse filter chamber as well as the unnecessary release of pollutants into the atmosphere. Thus, there is a long felt need for improved methods and systems for determining when a baghouse filter is leaking.

SUMMARY OF THE INVENTION

The present application thus may describe a method of detecting leaks in the filter bags of a baghouse filter chamber that includes determining when the filter bags have been cleaned and, during a post-cleaning period after the cleaning of the filter bags, determining whether the opacity level of the exhaust of the baghouse filter chamber exceeds a predefined opacity limit. The determining when the filter bags have been cleaned may include determining when the baghouse filter chamber has been released from isolation. The determining when the baghouse filter chamber has been released from isolation may include monitoring the status of an inlet valve of the baghouse filter chamber, an exit valve of the baghouse filter chamber, or both.

In some embodiments, the determining whether the opacity level of the exhaust of the baghouse filter chamber exceeds a predefined opacity limit may include monitoring the opacity level of the exhaust of the baghouse filter chamber with an opacity sensor during the post-cleaning period and comparing the opacity readings during the post-cleaning period with the value of the predefined opacity limit. The predefined opacity limit may be set within a range of about 5% to 15% opacity. In some embodiments, the predefined opacity limit may be about 10% opacity. The post-cleaning period may range in length from about 2 to 5 minutes. The post-cleaning period may begin immediately after the cleaning of the filter bags is completed and the baghouse filter chamber is released from isolation.

The method of also may include providing notification that an inspection of the filter bags or other corrective action should be done if an opacity reading during the post-cleaning period exceeds the predetermined opacity limit. In some embodiments, the methods may include determining whether the opacity level for previous post-cleaning periods exceeded the predefined opacity limit. The determining whether the opacity level for previous post-cleaning periods exceeded a predefined opacity limit may include determining if the opacity levels for the previous two post-cleaning periods exceeded the predefined opacity limit.

These and other features of the present invention will become apparent upon review of the following detailed description of the preferred embodiments when taken in conjunction with the drawings and the appended claims.

DETAILED DESCRIPTION OF EXEMPLARY EMBODIMENTS

Figure 1:
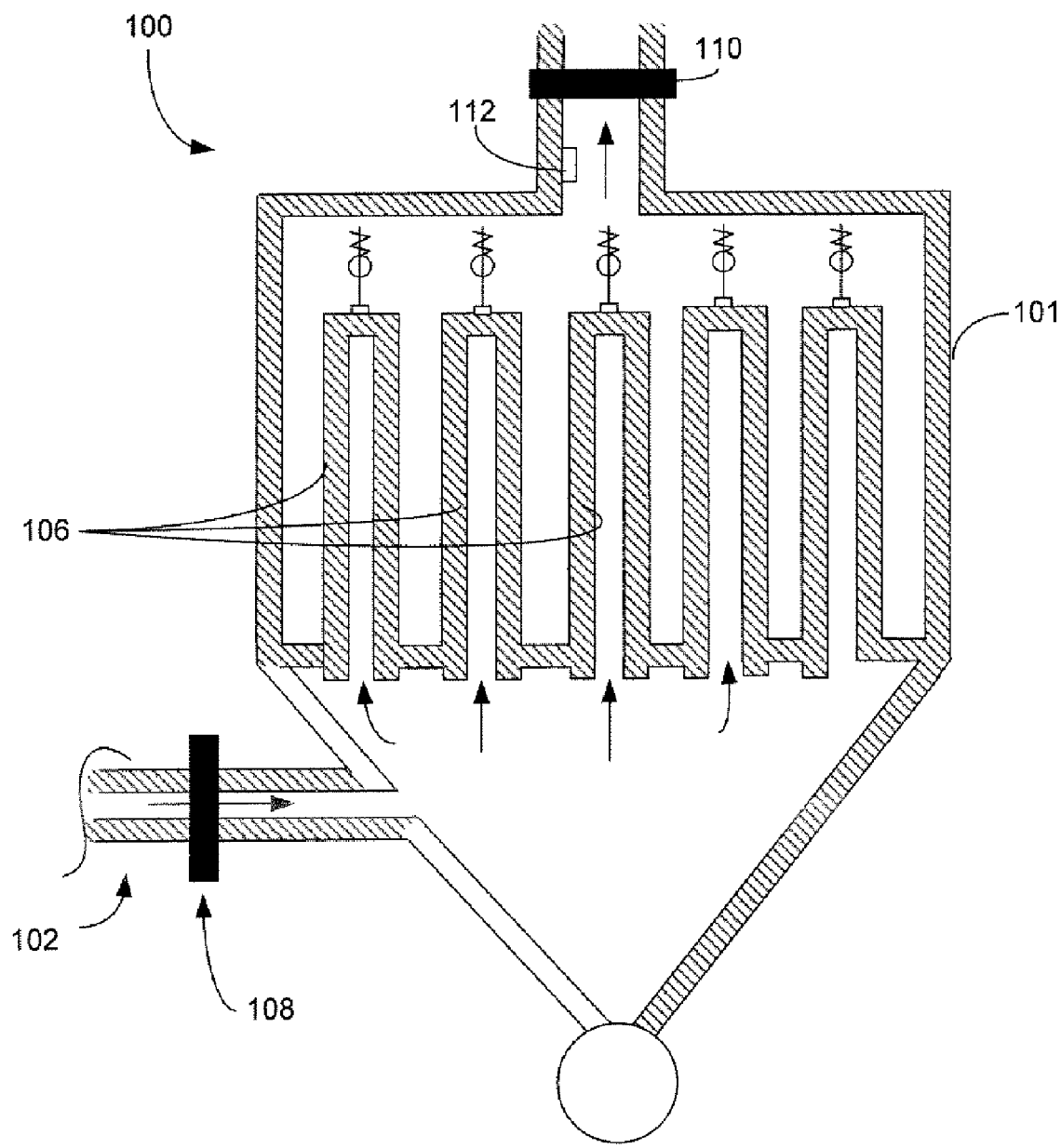
FIG. 1 is a cross-section view of a typical baghouse design in which an embodiment of the present invention may be used.

Referring now to the figures, where the various numbers represent like parts throughout the several views, FIG. 1 demonstrates an exemplary baghouse filter system 100 in which an embodiment of the present invention may be used. A baghouse filter chamber 101 may be disposed between an inlet flow pipe 102 and an exit flow pipe 104 for a fluid, such as air, which contains pollutants to be filtered out before discharge into the atmosphere. The baghouse filter chamber 101 may contain a plurality of filter bags 106. Arrows indicate the flow of air into the filter bags 106 in which fabric defines elongated bags closed at the top so that the air must flow through the fabric on its path to reach the exit flow pipe 104. In this manner, the air may be filtered by the filter bags 106.

The baghouse filter system 100 may further include an inlet valve 108 and an exit valve 110. The inlet valve 108 may be any of several known in the art and may act to open and close the inlet flow pipe 102. The inlet valve 108 may also include sensors known in the art which may report whether the inlet valve is open or closed to an operating system (not shown). The operating system, as discussed in more detail below, may be any known computerized or manual systems and/or devices known in the art that are used to operate the functioning of baghouse filter systems. Like the inlet valve 108, the exit valve 110 may be any of several known in the art and may act to open and close the exit flow pipe 104. The exit valve 110 may also include sensors known in the art which may report to the operating system whether the exit valve 110 is open or closed.

Periodically, the filter bags 106 of the baghouse filter chamber 100 must be cleaned. When this occurs, the inlet valve 108, the exit valve 110, or both may be closed, thus preventing the flow of air through the baghouse filter system 100. This is often referred to as "isolating" the baghouse filter chamber 101 for cleaning.

The exit flow pipe 104 may further include an opacity sensor 112 which may measure the opacity of the discharged air and report the measurement by methods known in the art to the operating system. Note that FIG. 1 demonstrates that the opacity sensor 112 measures opacity for a single baghouse filter chamber, baghouse filter chamber 101. As is known in the art, opacity sensors may be located in a more general exhaust location such that the opacity sensor 112 measures the opacity level of the exhaust from the several baghouse filter chambers of an entire system. The invention described herein may operate under either condition. The opacity sensor 112 may be any of those known in the art.

Figure 2:
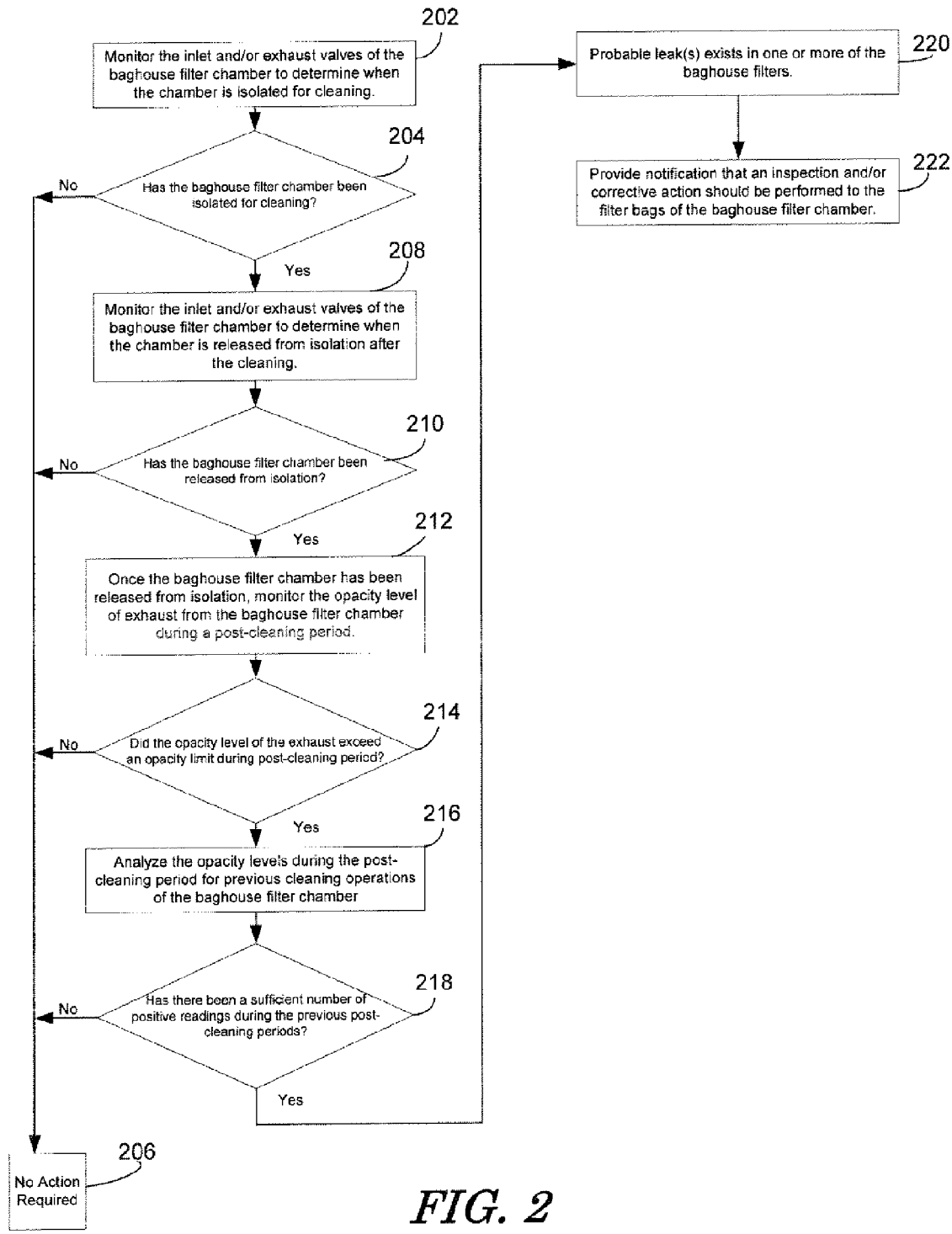
FIG. 2 is a flow diagram demonstrating an embodiment of the present invention.

FIG. 2 demonstrates a logic flow diagram 200 demonstrating an embodiment of the present invention. The flow diagram 200 may begin at block 202 where the process may monitor the inlet 108 and/or exhaust 110 valves of the baghouse filter system 100 to determine when the chamber 101 is isolated for cleaning. Generally, one or both of these valves are closed during the cleaning process, which may be detected and reported by sensors to the operating system.

At decision block 204, the process may determine from the monitoring of the inlet 108 and exhaust 110 valves whether the baghouse filter chamber 101 has been isolated for cleaning. If the answer to this question is "no," the process may continue to block 206 where it may be determined that no action is required. However, if the inquiry at block 204 yields a "yes" response, the process may continue to block 208.

At block 208, monitoring of the inlet 108 and/or exhaust 110 valves may continue so that it may be determined when the chamber 101 is released from isolation and the cleaning of the filter bags 106 is complete. At block 110, a determination may be made as to whether the baghouse chamber 101 has been released from isolation. This may be determined by using sensors known in the art and the operating system to sense when the baghouse chamber inlet 108 and/or exhaust 110 valves are opened and the chamber 101 is no longer isolated, i.e., air is allowed to pass through the baghouse filter chamber 101.

At block 212, once the baghouse filter chamber 101 has been released from isolation, opacity measurements of the exhaust may be taken, recorded and monitored during a post-cleaning period. As is known in the art, opacity is a measurement of the opaqueness of the exhaust being emitted from the baghouse filter chamber 101. As stated above, these measurements may be taken by opacity sensors. The post-cleaning period for monitoring the opacity level may range between 2-5 minutes in length, though this period may be significantly decreased or increased depending on the application.

At block 214 a determination may be made as to whether the opacity exceeded an opacity limit during the post-cleaning period. The opacity limit may signify the upper limit of opacity such that opacity measurements taken that are above this limit may indicate the presence of filter bag 106 leaks when the other conditions of this process are also satisfied. More specifically, a reading beyond the opacity limit during the post-cleaning period may be indicative of a condition where a filter bag 106 has leaks in it that have become exposed after the cleaning process. The build up of filtered soot or ash before the cleaning essentially plugged the leaks that had formed in the filter bag 106 and the cleaning of the filter bags 106 removed the blockage. Thus, an opacity reading during the post-cleaning period, which may be defined as a time period following a filter bag 106 cleaning that begins at some point after the cleaning and ends at a point when leaks may again be plugged by the build up of filtered soot or ash, may provide a true indication as to the status of the filter bags 106 in baghouse filter chamber. The reading also may determine whether or not the filter bags 106 are developing leaks or holes that might otherwise have gone unnoticed until a larger system failure takes place. Such failures may cause the emission of a significant amount of pollutants in the atmosphere and subject the plant to substantial governmental penalties if certain pollution limits are exceeded, and, thus, it is desirable that they be avoided. Further, in other embodiments, other rules may be used at this step to detect more severe leaks or provide an indication as to the severity of any leaks that may be present. For example, instead of requiring only that the opacity limit be exceeded once during the post-cleaning period, such a rule may require that the opacity limit be exceeded for 30 consecutive seconds of opacity readings (which, in some embodiments, may be taken at short intervals, such as every second or every half-second). Exceeding the opacity limit for 30 consecutive seconds may indicate a more severe leak.

For many applications, the opacity limit may be set between an opacity measurement of 5% and 15% opacity, though it may be significantly increased or decreased beyond this range depending on the specifics of the application. For some applications, the opacity limit of 10% may be used. If decision block 214 yields a "no" result, the process may continue to block 206 where it is determined that no action is required. As part of this step, the process may record the opacity readings obtained during the current post-cleaning period so that the readings may be referenced later. However, if block 214 yields a "yes" result (thus indicating that the opacity limit was exceeded during the post-cleaning period), the process may continue to block 216.

At block 216, the process may analyze the results of the opacity reading taken during the most recent post-cleaning period and opacity readings taken during previous post-cleaning periods. As part of this analysis, the process may determine at block 218 whether there have been a sufficient number of "positive" opacity readings (i.e., post-cleaning periods wherein the opacity limit was exceeded by at least one opacity reading) during the previous post-cleaning periods. If the determination at block 218 yields a "no" result, the process may continue to block 206 where it is determined that no action is required. However, if decision block 218 yields a "yes" result, the process may continue to block 220 where it is determined that there are probable leak(s) in one or more of the filter bags 106 in the baghouse filter chamber 101.

The number of previous "positive" opacity readings required for the process to proceed to block 220 may vary for different applications. For instance, the process may be allowed to proceed to block 220 after only the current positive opacity reading is taken, thus requiring no previous positive readings. However, for more accurate results, block 218 may require that at least 2 or 3 consecutive positive opacity readings be obtained before the process is allowed to proceed to block 220; thus, the process may look back at a few of the previous readings. Those of ordinary skill in the art will recognize that the number of consecutive positive opacity readings required by the process before a probable leak is identified may significantly vary. This variation may depend upon the specific application and the level of reliability desired by the plant operator. Further, those of ordinary skill will recognize that similar rules such as "positive readings in 3 out of the previous 4 post-cleaning periods" may be initiated at block 218 without deviating from the invention described herein.

At block 220, the process determines that a probable leak exists in one or more of the filter bags 106 of the baghouse filter chamber 101. At block 222, the process may provide notification that a probable leak exists and/or that an inspection of the filter bags 106 of the baghouse filter chamber 101 be performed, new bags installed, or other corrective action be taken. This notification may be provided in many different ways, such as, for example, an alarm, a computerized message, an email, an automatic message to a particular telephone number, a voicemail, a pager message, a text message, a fax, or other similar communication means.

Those of ordinary skill in the art will recognize the above-described process may be performed using the operating systems and/or the computerized or manual systems, software, and devices that are known in the art and already present at many plant locations. For example, a common management platform for manufacturing plant assets (i.e., the operating system of the plant) is System 1™ produced by Bently Nevada Corporation of Minden, Nev. In general, an operating system such as System 1™ may be configured such that it receives signals from the inlet 108 and exhaust 110 valves of baghouse filter systems 100 so that the state of these valves (i.e., whether they are opened or closed) may be monitored by the system. Signals from opacity sensors 112 also may be received and recorded by System 1™, which may also be configured to provide alerts, alarms, emails, computerized messages and the like to the operators of the system when certain conditions are satisfied. Further, such operating systems may have modules where such rules and procedures as described by the invention disclosed herein may be defined and initiated. An example of such a module in the System 1™ operating system is the Decision Support™ module. Of course, the invention described herein may be performed by many different types of operating systems, devices and the like, and the description of a particular example is not meant to be limiting. Those of ordinary skill in the art will recognize that the present invention may be used in all types of facilities that use baghouse and similar filter systems, including fossil fuel power generation facilities, cement manufacturing facilities, and others.

It should be apparent that the foregoing relates only to the preferred embodiments of the present invention and that numerous changes and modifications may be made herein without departing from the spirit and scope of the invention as defined by the following claims and the equivalents thereof.

What is claimed is:

1. A method of detecting leaks in the filter bags of a baghouse filter chamber, comprising:
   determining when the filter bags have been cleaned; and
   during a post-cleaning period after the cleaning of the filter bags, determining whether the opacity level of the exhaust of the baghouse filter chamber exceeds a predefined opacity limit.

2. The method of detecting leaks in the filter bags of a baghouse filter chamber according to claim 1, wherein the determining when the filter bags have been cleaned comprises determining when the baghouse filter chamber has been released from isolation.

3. The method of detecting leaks in the filter bags of a baghouse filter chamber according to claim 2, wherein the determining when the baghouse filter chamber has been released from isolation comprises monitoring the status of an inlet valve of the baghouse filter chamber, an exit valve of the baghouse filter chamber, or both.

4. The method of detecting leaks in the filter bags of a baghouse filter chamber according to claim 1, wherein the determining whether the opacity level of the exhaust of the baghouse filter chamber exceeds a predefined opacity limit comprises:
   monitoring the opacity level of the exhaust of the baghouse filter chamber with an opacity sensor during the post-cleaning period; and
   comparing the opacity readings during the post-cleaning period with the value of the predefined opacity limit.

5. The method of detecting leaks in the filter bags of a baghouse filter chamber according to claim 4, wherein the predefined opacity limit is set within a range of about 5% to 15% opacity.

6. The method of detecting leaks in the filter bags of a baghouse filter chamber according to claim 4, wherein the predefined opacity limit is about 10% opacity.

7. The method of detecting leaks in the filter bags of a baghouse filter chamber according to claim 1, wherein the post-cleaning period ranges in length from about 2 to 5 minutes.

8. The method of detecting leaks in the filter bags of a baghouse filter chamber according to claim 2, wherein the post-cleaning period begins immediately after the cleaning of the filter bags is completed and the baghouse filter chamber is released from isolation.

9. The method of detecting leaks in the filter bags of a baghouse filter chamber according to claim 1, further comprising providing notification that an inspection of the filter bags or other corrective action should be done if an opacity reading during the post-cleaning period exceeds the predetermined opacity limit.

10. The method of detecting leaks in the filter bags of a baghouse filter chamber according to claim 1, further comprising determining whether the opacity level for previous post-cleaning periods exceeded the predefined opacity limit.

11. The method of detecting leaks in the filter bags of a baghouse filter chamber according to claim 10, wherein the determining whether the opacity level for previous post-cleaning periods exceeded a predefined opacity limit comprises determining if the opacity levels for the previous two post-cleaning periods exceeded the predefined opacity limit.

12. The method of detecting leaks in the filter bags of a baghouse filter chamber according to claim 10, further comprising providing notification that an inspection of the filter bags or other corrective action should be done if the opacity readings during the current post-cleaning period and a predetermined number of previous post-cleaning periods exceeded the predetermined opacity limit.

13. A system for detecting leaks in the filter bags of a baghouse filter chamber, comprising:
   an opacity sensor for measuring the opacity of the exhaust of the baghouse filter chamber; means for determining when the filter bags have been cleaned; and
   means for recording the readings taken by the opacity sensor and comparing the readings to a predetermined opacity limit;
   wherein the system determines when the filter bags have been cleaned and, during a post-cleaning period after the cleaning of the filter bags, determines whether the opacity level of the exhaust of the baghouse filter chamber exceeds the predefined opacity limit.

14. The system for detecting leaks in the filter bags of a baghouse filter chamber according to claim 13, further comprising means for monitoring the status of an inlet valve, an exit valve, or both;

wherein the determining when the filter bags have been cleaned comprises monitoring the status of an inlet valve of the baghouse filter chamber, an exit valve of the baghouse filter chamber, or both to determine when the baghouse filter chamber has been released from isolation.

15. The system for detecting leaks in the filter bags of a baghouse filter chamber according to claim 13, wherein the predefined opacity limit comprises a range of about 5% to 15% opacity.

16. The system for detecting leaks in the filter bags of a baghouse filter chamber according to claim 13, wherein the predefined opacity limit comprises about 10% opacity.

17. The system for detecting leaks in the filter bags of a baghouse filter chamber according to claim 13, wherein the post-cleaning period ranges in length from 2 to 5 minutes.

18. The system for detecting leaks in the filter bags of a baghouse filter chamber according to claim 13, further comprising means for providing notification that an inspection of the filter bags or other corrective action should be done;

wherein the system provides notification that an inspection of the filter bags or other corrective action should be done if an opacity reading during the post-cleaning period exceeds the opacity limit.

19. The system for detecting leaks in the filter bags of a baghouse filter chamber according to claim 13, wherein the system further determines whether the opacity level for previous post-cleaning periods exceeded the predefined opacity limit.

20. The system for detecting leaks in the filter bags of a baghouse filter chamber according to claim 19, further comprising means for providing notification that an inspection of the filter bags or other corrective action should be done;

wherein the system provides notification that an inspection of the filter bags or other corrective action should be done if the opacity readings during the current post-cleaning period and a predetermined number of previous post-cleaning periods exceeded the opacity limit.

* * * * *